United States Patent [19]

Kautzky

[11] Patent Number: 4,612,011

[45] Date of Patent: Sep. 16, 1986

[54] CENTRAL OCCLUDER SEMI-BIOLOGICAL HEART VALVE

[76] Inventor: Hans Kautzky, 427 W. Blair, West Chicago, Ill. 60185

[21] Appl. No.: 516,315

[22] Filed: Jul. 22, 1983

[51] Int. Cl.⁴ ............................................... A61F 2/24
[52] U.S. Cl. ...................................................... 623/2
[58] Field of Search ................. 3/1.5, 1; 137/496, 859, 137/853

[56] References Cited

U.S. PATENT DOCUMENTS 3,176,712  4/1965  Ramsden ............................ 137/859
3,416,562 12/1968  Freeman .................................. 3/1.5

OTHER PUBLICATIONS

Hufnagel, et al., "Comparative Study of Cardiac and Vascular Implants in Relation to Thrombosis", vol. 61, No. 1, pp. 11–66, Jan. 1967.
"Prosthetic Replacement of the Aortic Valve", Sauvage et al., pp. 38–80.
"Mitral-valve Mechanics . . . ", Medical and Biological Engineering, Nov., 1973, pp. 691–702.
"Pressure Drop and Velocity Fields . . . ", European Society for Artificial Organs, 1983, pp. 3–20.
"Stress Analysis of Porcine Bioprosthetic Heart Valves in vivo", Journal of Biomedical Materials Research, vol. 16, pp. 811–825.

Primary Examiner—Richard J. Apley
Assistant Examiner—David Isabella
Attorney, Agent, or Firm—Hill, Van Santen, Steadman & Simpson

[57] ABSTRACT

A new prosthetic heart valve has a standard mounting ring with a centrally located occluder and a single piece biological circular flat membrane with a central aperture adapted to be selectively closed by the occluder.

The flexible membrane leans against the occluder in the closed position, and deflects axially away from the occluder when open. The occluder is held in position by spokes attached to the mounting ring, which also supports the membrane along its full periphery with one continuous readily accessible suture attachment.

3 Claims, 13 Drawing Figures

CENTRAL OCCLUDER SEMI-BIOLOGICAL HEART VALVE

BACKGROUND

1. Field of the Invention

The present invention relates to prosthetic heart valves and more particularly, to semi-biological heart valves consisting of mechanical structures together with parts made of biological material for optimal performance in vivo.

2. Prior Art

Prosthetic heart valves have been used for many years. The most common type of such valve incorporates a ball trapped in a cage. In recent years, other types of mechanical heart valves have been developed, which offer better flow characteristics than the ball in the cage type, but suffer from relatively high failure rates due to thrombus formation. This impairs the delicate motion of the various mechanical structures on which the functions of such valves depend. Some designs have a relatively high leak rate when closed; some produce high turbulence in the bloodstream; and nearly all cause damage to blood cells as a result of such cells being trapped and squeezed between the mechanical parts. As a result, nearly all patients using such valves are dependent on heparin.

Recently, valves incorporating purely biological materials have been successfully implanted, but the valves incorporating only biological material are very difficult to work with, and are subject to early failure when not installed in a particularly skillful manner.

Another promising design is a semibiological heart valve. Such a valve usually mimics the natural tricuspid heart valve and uses flexible biological material, formed either from real valve components or from other collageneous membranes. The structure of these valves is mechanical in nature, consisting of a metal or plastic ring, with posts, forming a platform to which the cusps are connected. The fabrication of such valves is very difficult, time consuming and expensive. The shape and position of all cusps must assure a good fit-tightness when closed, and the suture joints, by which the biological material is connected to the platform, must be very precise in order to provide a usefully long life for the valve.

The advantage of semi-biological valves is the gentleness with which they come to a closed position, so that few, if any, blood cells are damaged during valve closure. In addition, they are less noisy than purely mechanically arrangements.

However, the complicated shape is a disadvantage, not only in fabrication, but also in performance. If one cusp out of three stiffens up or deforms slightly, a minute thrombus formation gets lodged between the cusps and proper operation is thereafter impaired.

Although the semi-biological valves reduce the need for heparinization, which is crucially important, especially in the case of children, the small size valves required for children are the most difficult to be hand made because of their minute size and high complexity. The danger of thrombus formation is especially severe in the case of children, because thrombus retarding agents are usually contraindicated for children.

Recent studies have shown the deformation and stress of the collagenous materials of semi-biological valve components play an important role in their life expectancy before failure due to the delamination of the collagenous framework, producing cell infiltration and calcification. While the tension stresses in such a valve are well suited to the natural type of stress which collagen withstands, compression stresses, related often to bending of the cusps when opened, is extremely detrimental and most likely the primary cause for a series of a biological events ending in failure of such valves.

The natural valve has extremely thin leaflets in the cusps, making bending stresses very low. However, the prosthetic tricusp valve design is necessarily a compromise between strong and heavy leaflets for acceptable tension in the closed position, which are poor in bending stresses, or relatively thin ones which bend well but which are more inclined to fail in the suturing. The highly stress suture points at the corners of the cusps deliver most of the anchor forces, and the tricusp design offers no way out of this dilemma.

SUMMARY OF THE PRESENT INVENTION

A principal object of the present invention is to provide a semi-biological heart valve which is less delicate in its construction and which may be readily made in a variety of sizes, thereby reducing the need for heparinization of the recipient, irrespective of the sized valve required.

Another object of the present invention is to provide a semi-biological valve design which is simple and which produces a flow which is axially symetric and which has the relatively low pressure gradient.

A further object of the present invention is to provide a semi-biological heart valve design in which the stress is always in tension, thereby preventing the occurence of compression-caused deteriorization of its collgenous material. A further object of the present invention is to provide a semi-biological heart valve which has a small number of parts, and the minimum number of moving parts.

A further object of the present invention is to provide a semi-biological heart valve which reaches its closed position gently, thereby eliminating damage to blood cells during closure of the valve.

A further object of the present invention is to provide a heart valve in which the moving parts have very little inertia.

Another object of the present invention is to provide a semi-biological heart valve design in which the arrangement lends itself to the use of a robot during fabrication, to minimize the incidence and results of human errors during fabrication.

In one embodiment of the present invention, an axially symmetric occluder is provided, supported within a surrounding outer ring, and a flat circular biological membrane is secured to the outer ring, said membrane having a central circular aperture adapted to be selectively closed by the occluder.

The valve of the present invention achieves all of the aforementioned objects, and also achieves additional advantages. Among these is the fact that the membrane has very little travel required to go from fully opened to fully closed. The valve closes gently by leaning the free edge of the membrane against the occluder, resulting in local contact pressures between the membrane and the occluder and no damage to blood cells. The valve has virtually no regurgitation as it rests in its relaxed mode more than halfway toward the closed position. In operation it is practically noise free.

The valve of the present invention has its membrane mounted not in a set of single points, but rather along its largest dimension, which is its outer circumference and which is easily accessible.

In one design of the present invention, the membrane is attached to the mounting ring along a contact line with practically zero stress since there is no deformation at this location tangentially as well as radially.

Only tension stresses operate on the flat membrane, and since the membrane is flat and circular, it is relatively easy to fabricate out of biological material.

Stresses on the membrane are maintained at a low level, since the circular membrane is supported at its outer edge by suturing, and at its inner edge by leaning against the occluder.

In one arrangement of the present invention, all of the mechanical parts which are in contact with the blood are coated with biological tissue. This is not feasible in most other designs of semi-biological valves where such a coating would be destroyed by abrasion from the moving mechanical parts.

Other objects and advantages of the present invention will become manifest by an inspection of the following description and the accompanying drawings.

DESCRIPTION OF THE DRAWINGS

Reference will now be made to the accompanying drawings in which.

DESCRIPTION OF THE PREFERRED EMBODIMENT

Figure 1:
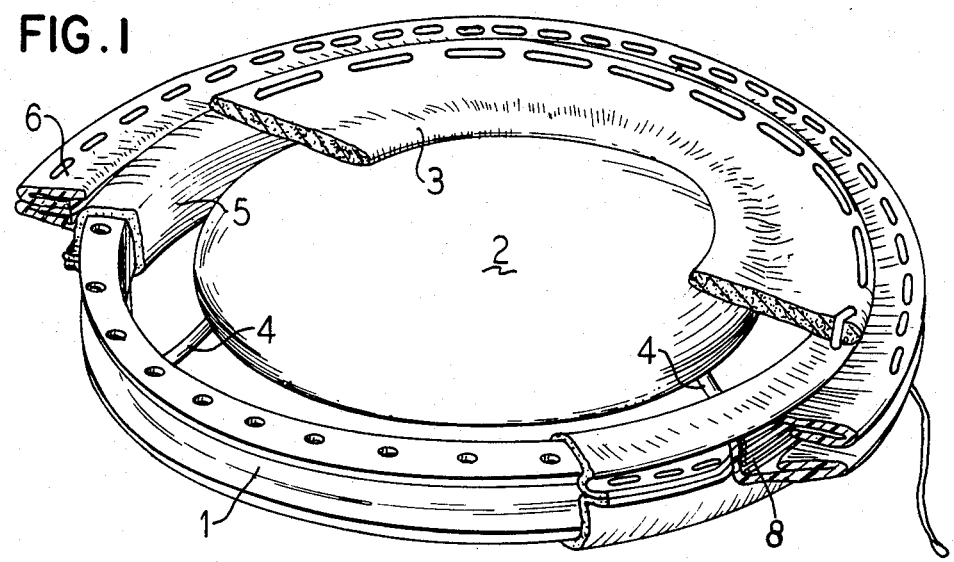
FIG. 1 is a perspective view of apparatus incorporating an illustrative embodiment of the present invention, with certain parts shown partially cut away for clarity.
Figure 2:
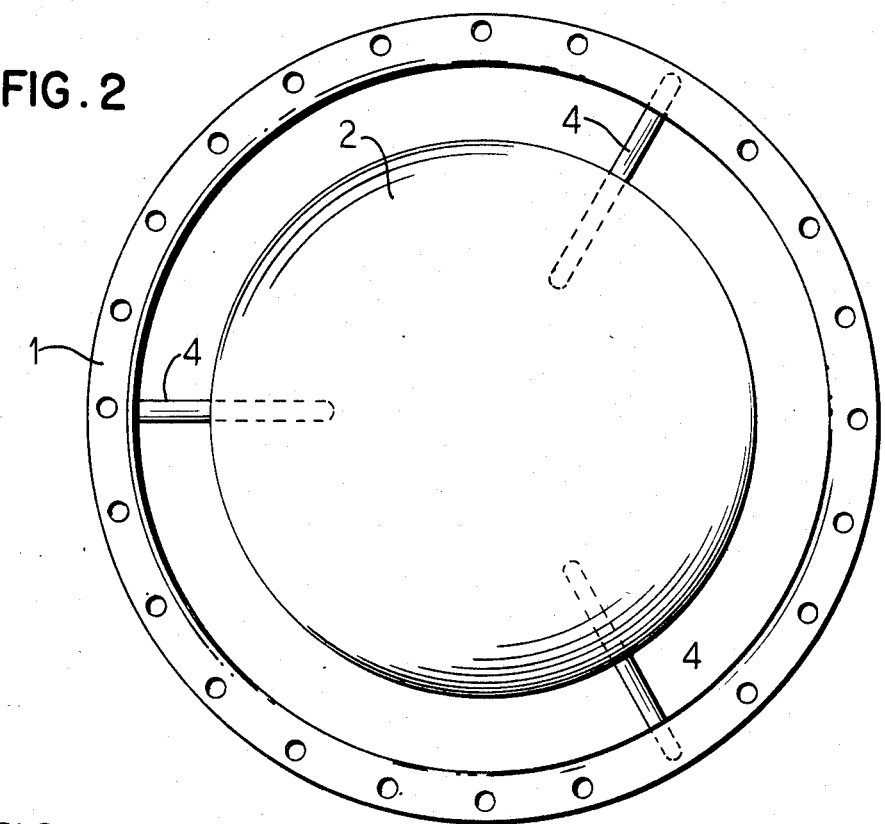
FIG. 2 is a plan view of the apparatus of FIG. 1.
Figure 3:
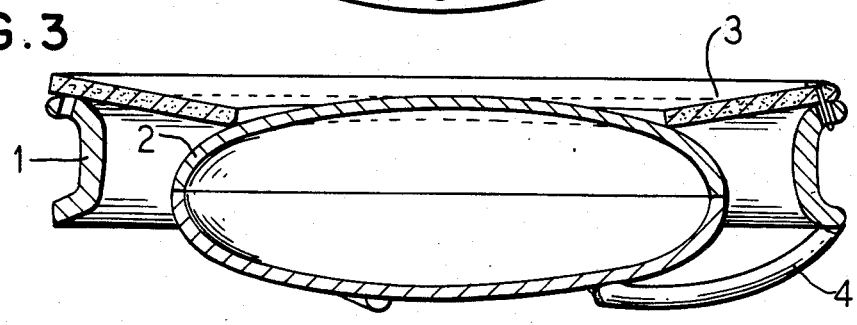
FIG. 3 is a transverse crossection of the apparatus of FIG. 1.

Referring to FIG. 1, a circular mounting ring 1 formed of metal or plastic has a U-shaped crossection, opening outwardly, defining upper and lower rims. The upper rim (as shown in FIG. 1) is provided with a series of equally spaced apertures which facilitate mounting of the membrane. A plurality of spokes 4 are attached to the outer ring and extend inwardly to support a central occluder 2. The occluder 2 is formed of metal or plastic and is circular and concentric with the ring 1, and oval in a transverse direction, as shown in FIG. 3. The occluder 2 is preferably hollow and may be formed of two hollow circular shells (one upper and one lower), welded or otherwise secured together. Alternatively, the lower shell may be omitted, but this complicates the coating of the occluder with an antithrombogenic skin. When plastic is used, the outer ring 1, the spokes 4 and the occluder 2 are preferably molded in one piece so that there are no seams. The occluder 2 may be solid, instead of hollow which is preferred when metal is used. Stainless steel is preferred when metal is used.

The ring 1 is covered with a sheath of antithrombogenic skin and a flat circular membrane 3 is sutured to the skin 5 through perforations in the upper rim of the ring 1. The membrane 3 has a central circular aperture, which is adapted to rest gently on the surface on the occluder 2. A woven dacron collar 6 is anchored by a band 8, formed of a wrapped dacron filament, to the outer surface of the ring 1, within the U-shaped cross section, and the free ends of the dacron band are sutured together so as to surround and enclose the band which supports the collar 6 on the ring 1. The dacron collar 6 is ideally suited for being incorporated into biological material such as the tissue surrounding the valve location.

The valve of the present invention satisfies simultaneously a number of different conditions. The overall mass of the valve is low, and it has a very short axial length, which makes it easier to install surgically. The valve makes a perfect seal when closed, and meets a number of different hydrodynamic criteria.

The design of the present invention lends itself to fabrication in a variety of sizes for accomodating patients with different size requirements.

The diameter of the occluder is critical. If it is too great in diameter, hydrodynamic resistance increases, but a minimum size is needed to give support to the biological membrane and to form a seal when closed. Although it is possible to arrive at the diameter of the occluder by hydrodynamic calculations, the interaction between the occluder and the elastic membrane is so great that the results of hydrodynamic calculations must be regarded as only approximate. It has been determined experimentally that 80%±10% of the inner diameter of the mounting ring is the preferred diameter.

The shape of the occluder is relatively noncritical except for the need for a large radius of curvature where it inneracts with the biological membrane. The large radius of curvature of this surface tends to aid in making the valve relatively flat in shape. A depth in the axial direction of 20% to 30% of the inner diameter of the mounting ring is preferred.

Figure 5:
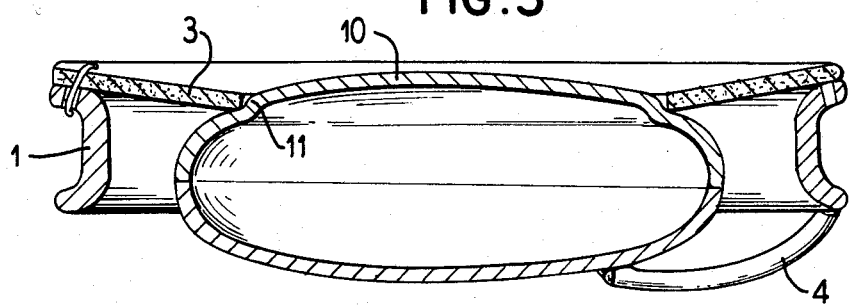
FIG. 5 is a transverse crossection of an alternative occluder member.

FIG. 5 illustrates, in crossection, an occluder 10 having a different crossection. The shape of the occluder is altered by incorporating an annular depression or step 11 in its surface, at the place where the inner end of membrane 3 contacts the occluder when the valve is in its closed position. This depression tends to assist centering the membrane, and tends to resist any asymetrical movement of the membrane relative to the occluder which may result from some local characteristic of the membrane. The depth of the depression is preferably about equal to the thickness of the membrane.

The thickness of the membrane may be specified by consideration of the maximum strain, and the capacity of the material in tension. The location of the maximum stress is the inner circumference of the orifice, and the direction is tangential. Its thickness is preferably about 1% to 5% of the inner diameter of the ring 1. Radial stress at this point is zero.

The membrane is formed of collagenous biological matter such as dura matter, pericardium material or sclera material. The sclera material offers the advantage of anisotropic fiber orientation, but must be reduced in thickness for best results.

The diameter of the central orifice of the membrane is difficult to calculate theoretically, because the biological material is very flexible, and changes size with load, moisture, and condition of handling. Experimental test results have shown that the best orifice size to be 64%±10% of the inner diameter of the mounting ring 1. This diameter is the most sensitive dimension of the valve and is responsible almost solely for the overall hydrodynamic resistance of the valve in its open position.

The hydrodynamic interaction of the fixed occluder and the flexible membrane increases sharply in proportion to their relative proximity. This relation is very steep and asymptotic. A close proximity is needed because the membrane elastically stretches to make contact with the occluder in order to block reverse flow. Experimental results have shown that an optimum axial distance of membrane to occluder is about 4% to 8% of the inner diameter of the mounting ring 1. This dimension is measured axially between the plane of the upper rim of the mounting ring 1, to the plane of the circle of contact between membrane and the occluder. Thus the movement from rest to closed position is only 4% to 8% of the inner diameter. Movement from rest to open position is somewhat more because there is no restraint on the downstream side of the membrane.

The parameter of the amount of travel in the moving parts between open and closed position is a critical one. This is because a truly passive valve changes its position only after the liquid medium that it controls has reversed its directional flow. Little or no change occurs in the short time during which the flow rate is zero. If a large amount of travel is required for the moving member to close the valve, then the time of reverse flow is relatively long, and the reverse velocity reaches a relatively high level, causing the loss of available pumping power and regurgitation. This is true even if one assumes that no leakage occurs once the valve is closed. The increase of speed in the reverse direction has a kinematic consequence as well, producing a pressure dip in the discharge pattern and a dramatic increase of kinetic energy of the column of blood in the aortic passage. Here the elastic walls provide the necessary stored energy for producing reverse acceleration. When the valve finally closes, the hydrodynamic shock creates severe stresses, and causes oscillation to occur, which produce fatigue and a tendency toward thombus formation at points where there are high concentrations of stress in the surrounding tissue. This leads to calcification or even outright mechanical failure. Mechanical valves are particularly poor performers in this respect, since the mass of a relative large ball has an inertia which delays its closing motion. This inertia is added, when closing, to the inertia of the reverse flowing fluid, resulting in a large dynamic impact on the valve seat during closure.

When it is desired to minimize the length of travel of the moving valve member, controlling the flow in the center of a conduit, close to its axis, is a relatively poor choice. The present invention takes a different approach, and attempts to control flow at the periphery, where most of the crossectional area is located, rather than at any point close to the axis of the flow. Since most of the crossection is located at the periphery, (due to the quadratic relationship between radius and area in a circular channel) the design of the present valve is in position to directly control at a greater proportion of the flow. Since a valve of the present invention tends to control flow near the outer periphery of the flow, a much smaller movement is required between open and closed positions, yielding a markedly advantageous operation. The reduction in required movement, and the corresponding reduction in the time of the reverse flow, results in a marked reduction in the kinetic energy of the column of blood within the aortic chamber. This is because the maximum reversed speed is held to a low value, and kinetic energy is a function of the square of the speed.

The valve of the present invention is axially symmetric, which tends to minimize flow turbulence, and provides lower hydrodynamic resistance. All components of the valve are axially symmetric and the small number of components, and the simplicity of construction of the present valve are also important advantages.

The manufacture of valves in accordance with the present invention is facilitated since only flat circular biological materials are required, which are relatively simple to cut and mount, thus reducing the cost while at the same time improving quality and reliability.

When a circular flat disc is deformed axially, it experiences only stresses in tension, provided that it is thin and supported on its outer edge. This is extremely important, because biological matter has poor tolerance for compression. The design of the present invention, by eliminating compression stresses, increase greatly the fatigue life of the membrane, and the short travel of the membrane between open and closed positions yields the advantages described above. Also, the soft landing of the membrane on the occluder, and the low specific pressure in the seat area, eliminates damage to blood cells, and avoids the need for heparinization. The valve design of the present invention has a superior ability to dampen oscillations which is also an improved operational characteristic.

FIG. 4 illustrates in parts a to i, a number of steps to be followed in the fabrication of a heart valve incorporating the present invention. FIG. 4a illustrates an antithrombogenic skin, which has been cut in three places to accomodate the spokes which support the central accluder. FIG. 4b shows in perspective the antithombogenic skin surrounding the occluder, with three seams leading from the spokes to a central point where they meet. FIG. 4c shows a plan view from an upstream perspective.

Figure 4A:
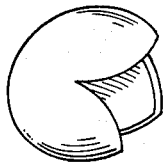
FIG. 4, comprising parts a to i illustrates a sequence of steps showing how the mechanical parts may be coated with biological tissue.
Figure 4B:
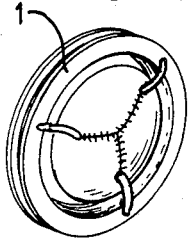
Figure 4C:
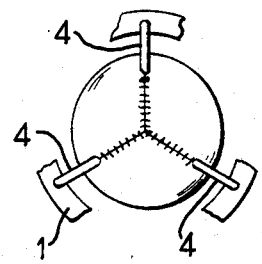
Figure 4D:
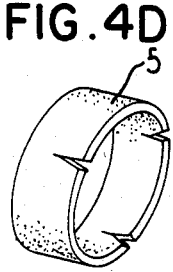
Figure 4E:
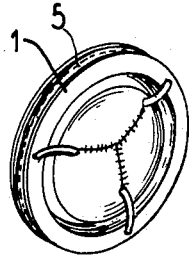
Figure 4F:
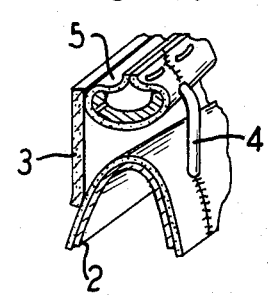

FIG. 4d shows an antithrombogenic skin adapted to surround the mounting ring 1, which skin has been slit in three places to accomodate the spokes. FIG. 3e shows the mounting ring with the skin surrounding it, with the free edges of the skin stitched together at its outer periphery. FIG. 4f shows in perspective and crossection a spoke 4, the occluder 2 (in crossection), and the mounting ring 1 (in crossection), with the antithrombogenic skin surrounding the outer ring in having it stitched together. The membrane 3 is also shown in crossection in FIG. 4f, and is stitched to the antithrombogenic skin through the perforations in the support ring.

Figure 4G:
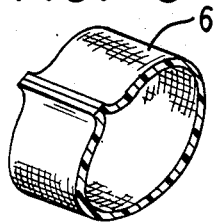
Figure 4H:
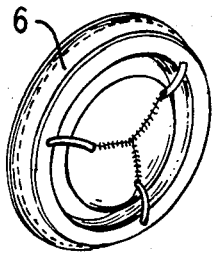
Figure 4I:
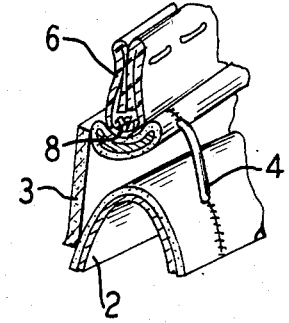

FIG. 4g shows a strip of dacron material which has been sewn together so as to form a ring, and FIG. 4h shows a perspective view of the finished valve after the dacron ring has been seated in the groove of the support ring, and with its outer peripheral edges stitched together. FIG. 4i illustrates a perspective view partly in crossection. As shown in FIG. 4i, the dacron ring is held in position in the mounting ring by a band formed of several windings of dacron fiber 12. As shown in FIG. 4i, six turns of the dacron fiber are employed. The free ends of this fiber (not shown) are then knotted together to firmly secure the dacron relative to the mounting ring.

The valve of the present invention lends itself to assembly by robot, thus eliminating human errors in assembly. The regular apertures in the mounting ring, together with the planar membrane orientation and the regular circular suturing required minimizes the complexity of robot apparatus and programming required. Thus a more uniform and reliable product is produced.

Although the present invention has been described in connection with a fixed central occluder semi-biological heart valve, the principals of the present invention are equally applicable to other heart valves prostheses, without departing from the present invention. Various other modifications and/or rearrangements will become apparent to those skilled in the art without departing from the central features of novelty of the present invention, which are intended to be defined and secured by the appended claims.

What is claimed is:

1. A semi-biological heart valve prosthesis comprising a mounting ring, said mounting ring having a plurality of inwardly directed spokes, a central occluder connected to and supported by said spokes, and a flat circular anti-thrombogenic membrane connected to said mounting ring along its outer circumference by suturing, said membrane having an aperture adapted to be selectively closed by said occluder, said central occluder being circular and having a diameter of 80%±10% of the inner diameter of the mounting ring, and is oval shaped in cross-section and approximately 20% to 30% wide axially in relation to said inner diameter.

2. The semi-biological heart valve prothesis according to claim 1, wherein said occluder has an annular depression at the line of contact with said membrane, the depth of said depression being approximately equal to the thickness of said membrane.

3. A semi-biological heart valve prosthesis comprising a mounting ring, said mounting ring having a plurality of inwardly directed spokes, a central occluder connected to and supported by said spokes, and a flat circular anti-thrombogenic membrane connected to said mounting ring along its outer circumference by suturing, said membrane having an aperture adapted to be selectively closed by said occluder, said membrane being formed of a flat piece of collagen tissue with a thickness of 1% to 5% of the inner diameter of the mounting ring and said aperture is 64%±10% of the inner diameter of said ring.

* * * * *